United States Patent
Aggerholm et al.

(10) Patent No.: US 10,252,036 B2
(45) Date of Patent: Apr. 9, 2019

(54) THROMBUS REMOVAL APPARATUS AND METHOD

(71) Applicant: COOK MEDICAL TECHNOLOGIES LLC, Bloomington, IN (US)

(72) Inventors: Steen Aggerholm, St. Heddinge (DK); Kian Olsen, Vallensbaek Strand (DK)

(73) Assignee: COOK MEDICAL TECHNOLOGIES LLC, Bloomington, IN (US)

( * ) Notice: Subject to any disclaimer, the term of this patent is extended or adjusted under 35 U.S.C. 154(b) by 700 days.

(21) Appl. No.: 13/718,445

(22) Filed: Dec. 18, 2012

(65) Prior Publication Data
US 2013/0158511 A1 Jun. 20, 2013

(30) Foreign Application Priority Data
Dec. 19, 2011 (GB) .................................. 1121788.2

(51) Int. Cl.
*A61M 25/10* (2013.01)
*A61B 17/3207* (2006.01)
*A61B 17/22* (2006.01)

(52) U.S. Cl.
CPC ........... *A61M 25/104* (2013.01); *A61B 17/22* (2013.01); *A61B 17/3207* (2013.01); *A61B 17/320725* (2013.01); *A61B 2017/22061* (2013.01); *A61B 2017/22067* (2013.01); *A61B 2017/22079* (2013.01); *A61B 2017/22084* (2013.01); *A61M 25/1002* (2013.01); *A61M 2025/109* (2013.01); *A61M 2025/1052* (2013.01)

(58) Field of Classification Search
CPC ........ A61M 25/104; A61M 2025/1004; A61M 2025/109; A61M 2015/1004; A61M 2015/109; A61M 25/1002; A61M 2025/1052; A61B 17/3207; A61B 17/320725; A61B 17/22; A61B 2017/22084; A61B 2017/22061; A61B 2017/22079; A61B 2017/22067
USPC ......................... 604/96.01, 103.07, 506, 509
See application file for complete search history.

(56) References Cited

U.S. PATENT DOCUMENTS 4,406,653 A * 9/1983 Nunez ............... A61M 25/1034
604/103
5,011,488 A 4/1991 Ginsburg
(Continued)

FOREIGN PATENT DOCUMENTS

WO    WO 99/23952    5/1999
WO    WO 99/39648    8/1999
(Continued)

*Primary Examiner* — Kevin C Sirmons
*Assistant Examiner* — Tiffany Legette-Thompson
(74) *Attorney, Agent, or Firm* — Brinks Gilson & Lione (57) ABSTRACT

Thrombus removal apparatus includes a balloon catheter with a short balloon at a distal end thereof. An aspiration catheter is disposed coaxially over the balloon catheter. The balloon catheter includes a plurality of holes for the administration of lytic agent. The apparatus does not seal off completely the zone of the vessel around the thrombus, thereby allowing movement of blood within the vessel. The balloon is shaped so that it can be pulled along the vessel in an upstream direction so as to drag against the vessel walls for assisting in the removal of the thrombus.

16 Claims, 5 Drawing Sheets

(56) References Cited

U.S. PATENT DOCUMENTS

| | | |
|---|---|---|
| 6,159,230 A | 12/2000 | Samuels |
| 6,179,860 B1 | 1/2001 | Fulton, III et al. |
| 6,217,548 B1 | 4/2001 | Tsugita et al. |
| 6,221,006 B1 | 4/2001 | Dubrul et al. |
| 6,238,412 B1 | 5/2001 | Dubrul et al. |
| 6,325,816 B1 | 12/2001 | Fulton, III et al. |
| 6,409,742 B1 | 6/2002 | Fulton, III et al. |
| 6,530,923 B1 | 3/2003 | Dubrul et al. |
| 6,602,204 B2 | 8/2003 | Dubrul et al. |
| 6,602,265 B2 | 8/2003 | Dubrul et al. |
| 6,695,858 B1 | 2/2004 | Dubrul et al. |
| 6,699,260 B2 | 3/2004 | Dubrul et al. |
| 6,758,855 B2 | 7/2004 | Fulton, III et al. |
| 7,479,152 B2 | 1/2009 | Fulton, III et al. |
| 7,491,210 B2 | 2/2009 | Dubrul et al. |
| 2001/0011182 A1 | 8/2001 | Dubrul et al. |
| 2002/0062119 A1 | 5/2002 | Zadno-Azizi et al. |
| 2002/0143359 A1 | 10/2002 | Fulton, III et al. |
| 2003/0109896 A1 | 6/2003 | Dubrul et al. |
| 2003/0199890 A1 | 10/2003 | Dubrul et al. |
| 2004/0010206 A1 | 1/2004 | Dubrul et al. |
| 2004/0073194 A1* | 4/2004 | Olsen ................ A61M 25/00 |
| | | 604/537 |
| 2004/0082965 A1* | 4/2004 | Beckham ............ A61L 29/126 |
| | | 606/192 |
| 2004/0199202 A1 | 10/2004 | Dubrul et al. |
| 2004/0243171 A1 | 12/2004 | Fulton, III et al. |
| 2004/0260332 A1 | 12/2004 | Dubrul et al. |
| 2004/0260333 A1 | 12/2004 | Dubrul et al. |
| 2005/0033172 A1 | 2/2005 | Dubrul et al. |
| 2005/0065469 A1 | 3/2005 | Tal et al. |
| 2005/0075661 A1* | 4/2005 | Levine ................ A61M 25/008 |
| | | 606/194 |
| 2005/0245894 A1* | 11/2005 | Zadno-Azizi .... A61B 17/12045 |
| | | 604/509 |
| 2006/0149308 A1* | 7/2006 | Melsheimer ... A61B 17/320725 |
| | | 606/192 |
| 2006/0161103 A1* | 7/2006 | Constantz et al. ....... 604/101.04 |
| 2007/0225677 A1* | 9/2007 | Rowe et al. ................... 604/509 |
| 2007/0232996 A1* | 10/2007 | Andersen ................ A61F 2/958 |
| | | 604/103.02 |
| 2008/0086083 A1* | 4/2008 | Towler .................. A61L 29/126 |
| | | 604/103.06 |
| 2008/0136059 A1* | 6/2008 | Yoshino ................ A61L 29/041 |
| | | 264/299 |
| 2009/0187144 A1* | 7/2009 | Jayaraman ........ A61M 25/1002 |
| | | 604/103.02 |
| 2009/0321010 A1* | 12/2009 | Yoshino et al. .............. 156/290 |
| 2010/0030256 A1 | 2/2010 | Dubrul et al. |
| 2010/0114113 A1 | 5/2010 | Dubrul et al. |
| 2011/0046542 A1 | 2/2011 | Evans et al. |
| 2011/0245665 A1* | 10/2011 | Nentwick ............ A61M 1/285 |
| | | 600/433 |
| 2013/0110152 A1 | 5/2013 | Dubrul et al. |

FOREIGN PATENT DOCUMENTS

| | | |
|---|---|---|
| WO | WO 00/74561 A1 | 12/2000 |
| WO | WO 2004/093966 A1 | 11/2004 |
| WO | WO 2011/112340 A1 | 9/2011 |

\* cited by examiner

THROMBUS REMOVAL APPARATUS AND METHOD

CROSS-REFERENCE TO RELATED APPLICATIONS

This application is related to and claims the benefit of priority to GB 1121788.2, filed on Dec. 19, 2012 which is incorporated herein by reference in its entirety.

TECHNICAL FIELD

The present invention relates to thrombus removal apparatus and to a method of removing a thrombus from a patient.

BACKGROUND ART

There are established procedures for removing thrombi from a patient's vasculature by percutaneous insertion of appropriate treatment apparatus into the vasculature of the patient. A procedure which is well documented involves the use of an assembly which includes a balloon catheter provided with two inflatable balloons which are spaced from one another at the distal end of the catheter. The balloon catheter is inserted endoluminally into the patient's vasculature until the balloons are located either side of a thrombus to be removed. The balloons are then inflated so as to close off that part of the patient's vessel. The assembly includes provision for feeding into the space between the two inflated balloons a thrombolytic or other lytic agent, typically through a lumen of the balloon catheter. The thrombolytic agent will dissolve the thrombus located between the two inflated balloons, whereupon the dissolved thrombus material can be removed, typically by aspiration. Particularly when a thrombus is established, that is when the thrombus is dense and well set, it can take a significant time to dissolve the thrombus and thus remove this from the patient.

Examples of thrombus treatment apparatus can be found, for example, in U.S. Pat. No. 5,279,546, U.S. Pat. No. 5,059,178 and U.S. Pat. No. 5,925,016.

DISCLOSURE OF THE INVENTION

The present invention seeks to provide improved thrombus removal apparatus and an improved method of removing a thrombus from a patient's vasculature.

According to an aspect of the present invention, there is provided thrombus removal apparatus for removing a thrombus from a patient's vasculature, the apparatus including: a carrier catheter having a distal end and a proximal end, a single or singular occlusion device fixed to or proximate the distal end of the catheter, at least one supply element located proximal of said distal end of the carrier catheter for supplying a bioactive agent, and a retrieval element located proximal of said distal end of the carrier catheter for retrieving thrombus material from a patient's vasculature, wherein the occlusion device is expandable to occlude solely said distal end of the carrier catheter.

Conventional thrombus removal apparatus generally seeks to isolate the area of the thrombus prior to the administration of a thrombolytic agent, in order to prevent the seepage or transfer of the thrombolytic agent to other parts of the patient's system, in particular to the whole of the patient's bloodstream. Isolation can be achieved by a double balloon arrangement in which the balloons are positioned either side of a thrombus to be treated and inflated to close off that part of the patient's lumen. Such isolation prevents undesired effects on the patient and allows for the use of more concentrated doses of thrombolytic agent. However, the inventors have found that isolating a thrombus in this manner causes stagnation of blood in the isolated region, which can cause a lengthening of the time required to breakdown the thrombus. By contrast, the apparatus taught herein does not entirely isolate the thrombus from the patient's bloodstream as the space proximal of the occlusion device remains open to the patient's bloodstream, such that there will continue to be some movement, or turbulence, of blood around the thrombus caused by the natural pumping and movement of the patient's circulatory system. This can assist in speeding up the breakage of thrombus material, particularly when this is well established. Thus, the structure taught herein could be said to occlude the vessel one side (preferably downstream) of the thrombus and to leave the other side (preferably upstream) exposed to the patient's blood stream.

Furthermore, the apparatus taught herein can act to scrape a thrombus from a vessel wall, which again can speed up the process of removal of the thrombus. A combination of thrombolytic agent administered with the taught apparatus and scraping of the thrombus can lead to much faster removal of a thrombus than with prior art devices.

In the preferred embodiment, the occlusion device includes at least one balloon and the carrier catheter is a balloon catheter.

Advantageously, the supply element includes at least one port in the carrier catheter, preferably a plurality of ports. The ports may be spaced longitudinally along the carrier catheter and/or may be angularly spaced around the catheter. For this purpose, the carrier catheter may include at least one fluid supply lumen for supplying bioactive agent in fluid form to the port or ports.

It is preferred that the retrieval element is an aspiration catheter, which is preferably moveable relative to the carrier catheter, useful particularly in removing smaller thrombi or remaining thrombus material.

In a preferred embodiment, the balloon has a longitudinal dimension and is rounded in said longitudinal direction when inflated, for example when inflated having a doughnut shape, particularly a diameter greater than a length thereof. This form of balloon, it has been found, is particularly effective for scraping thrombus material from the walls of a patient's vessel. More specifically, vessel walls tend not to be smooth, particularly when a thrombus is attached thereto. This shape of balloon is able to deform and flex so as to remain in constant contact with the lumen wall and therefore in a sealing configuration.

Thus, it is preferred that the balloon is designed to scrape against a vessel wall when inflated thereby to scrape thrombi from the vessel wall.

In some embodiments, a longitudinal axis is defined by the carrier catheter, and the balloon has first and second ends, separated by a longitudinal distance.

Reference to the diameter of the balloon can be considered to be reference to the maximum diameter of the balloon, in a direction transverse to, and preferably perpendicular to, the longitudinal axis.

When inflated, a radius of the balloon can taper, in preferably a linear fashion, from a radially outermost section to the first and second ends of the balloon. Such a shape provides an improved scraping effect as it provides an effectively pointed cross-section.

Additionally, the radially outermost section of the balloon may be provided with a circumferential flange to act as a scraper along the walls of a vessel. This can provide a particularly effective scraping action analogous to a windscreen wiper.

The flange can be inflatable, preferably by being part of the balloon so that the balloon and the flange together enclose a single inflatable chamber.

A thickness of the wall of the flange is preferably the same as a thickness of the wall of the balloon.

The balloon can include one or more strengthening elements, which can be one or more layers of fibrous or woven material.

The balloon can include one or more scoring or cutting elements.

In an embodiment, the carrier catheter and the aspiration catheter are concentrically arranged, the aspiration catheter being located over the carrier catheter. Advantageously, the carrier catheter is able to be located substantially entirely within the aspiration catheter. Preferably, the aspiration catheter acts as a delivery sheath for the endoluminal positioning of the carrier catheter.

According to another aspect of the present invention, there is provided a method of removing a thrombus from a vessel by means of thrombus removal apparatus, which apparatus includes a carrier catheter having a distal end and a proximal end, a single occlusion device fixed to or proximate the distal end of the catheter, at least one supply element located proximal of said distal end of the carrier catheter for supplying a bioactive agent, and a retrieval element located proximal of said distal end of the carrier catheter for retrieving thrombus material from a patient's vasculature, wherein the occlusion device is expandable to occlude solely said distal end of the carrier catheter; the method including the steps of:

inserting the distal end of the thrombus removal apparatus endoluminally into a patient such that the distal end of the carrier catheter is located downstream of a thrombus to be removed;

deploying the occlusion device so as substantially to close fluid flow downstream of the thrombus;

injecting bioactive agent through the at least one port, thereby to initiate or cause breakup of the thrombus;

moving the occlusion device in an upstream direction; and removing thrombus material via the retrieval element.

Advantageously, the occlusion device is a balloon, the method including the step of inflating the balloon and then moving the balloon in an upstream direction.

According to an aspect of the invention, there is provided a method of removing a thrombus from a vessel by means of thrombus removal apparatus, which apparatus includes a balloon catheter having a proximal and a distal end, a balloon attached to or proximate the distal end of the balloon catheter, an aspiration catheter, and at least one supply element for supplying proximate the balloon a bioactive agent; the method including the steps of:

inserting a distal end of the thrombus removal apparatus endoluminally into a patient such that the distal end of the balloon catheter is located beyond a thrombus to be removed;

inflating the balloon so as substantially to close fluid flow beyond the thrombus;

injecting bioactive agent through the at least one port, thereby to initiate or cause breakup of the thrombus;

moving the inflated balloon in a proximal direction;

applying aspiration to the aspiration catheter; and aspirating the thrombus into the aspiration catheter.

The distal end of the balloon can be positioned downstream or upstream of the thrombus.

Preferably, aspiration is applied during movement of the deployed occlusion device.

According to another aspect of the invention, there is provided a thrombus removal apparatus, the apparatus including a delivery sheath and a plurality of carrier catheters, each carrier catheter having a distal end and a proximal end and defining a longitudinal axis; each carrier catheter including a singular occlusion device fixed to or proximate the distal end of the catheter, and at least one supply element located proximal of said distal end of the carrier catheter for supplying a bioactive agent; the apparatus further including a retrieval element to be located proximal of said distal end of one of the carrier catheters for retrieving thrombus material from a patient's vasculature; wherein the occlusion device of each catheter includes a balloon having a length in the direction of the longitudinal axis and which is expandable to occlude a vessel solely at or proximate said distal end of the carrier catheter, wherein the balloon is rounded in the direction of the longitudinal axis when inflated, and wherein the balloon has first and second ends separated by a distance such that when inflated the balloon has a diameter which is greater than the length of the balloon, wherein each of the plurality of carrier catheters includes a different sized balloon to allow a carrier catheter to be selected which is matched to a size of a vessel into which it is to be inserted.

The features of the different aspects above can be combined and/or interchanged.

BRIEF DESCRIPTION OF THE DRAWINGS

Embodiments of the present invention are described below, by way of example only, with reference to the accompanying drawings, in which.

DESCRIPTION OF THE PREFERRED EMBODIMENTS

There are shown in the accompanying drawings preferred embodiments of thrombus treatment apparatus. It will be appreciated that only the principal components of the apparatus are shown in the drawings and described below and that other components of the apparatus will be well known to the person skilled in the art and are therefore not described herein in any detail. The assembly will particularly include, thus, the components of a standard introducer assembly such as a guide wire, a carrier sheath, an external manipulation unit coupled to the carrier sheath and having one or more haemostatic valves as well as couplings for flushing fluid and the like. The components will typically include those used for the commonly performed Seldinger technique for introducing the thrombus removal apparatus percutaneously into the patient.

It will also be understood that the features depicted in the drawings are not necessarily to scale and have been drawn preliminary with clarity of disclosure in mind.

The embodiments described below use as the occluder a balloon. This is the preferred implementation and the structure does not preclude other types of occluder.

Figure 1:
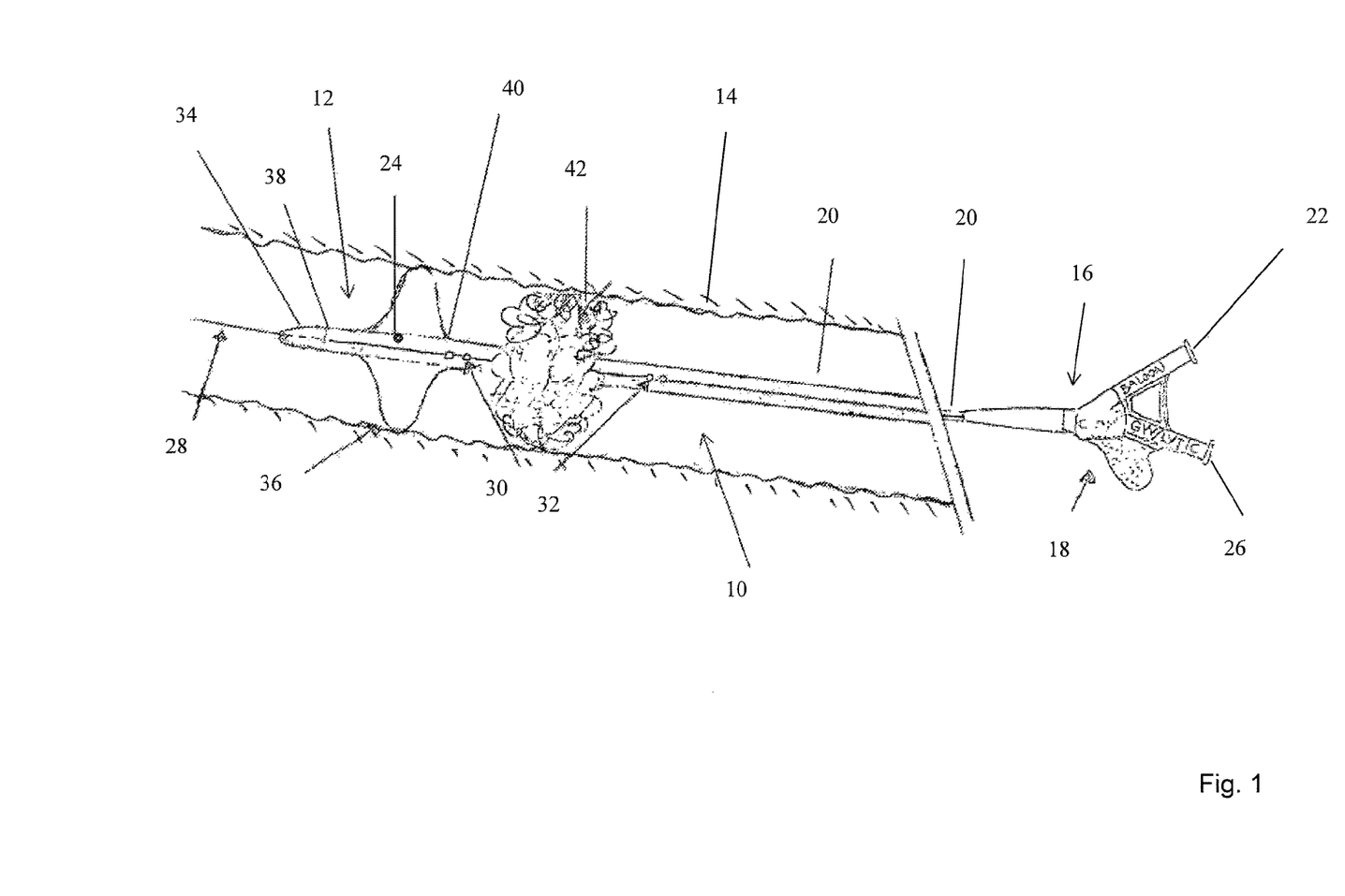
FIG. 1 is a schematic diagram of an elevational view of a part of an embodiment of thrombus removal apparatus.

Referring first to FIG. 1, there are shown the principal components of a thrombus removal apparatus 10 of which the distal end 12 is shown located within a vessel 14 of a patient. The apparatus 10 includes at a proximal end 16 a Y-fitting 18 which is fixed to a carrier catheter 20. The catheter 20 is, in this example, provided with at least two lumens therewithin which extend from the Y-fitting 18 to the distal end 12 of the assembly 10. The Y-fitting 18 includes a Luer fitting 22 which feeds into a lumen of the catheter 20 and to at least one inflation port 24 in the catheter at distal end 12 thereof.

The Y-fitting 18 also includes a second Luer fitting 26 which is coupled to a second lumen in the catheter 20, which lumen extends all the way to the extremity of the catheter 12 and which is able to accommodate a guide wire 28 of conventional type. This lumen of the catheter 20 is also provided with one or more apertures or ports 30, 32 within the wall of the catheter 20, for the administration of lytic, specifically thrombolytic, agent through the catheter 20 supplied via the Luer fitting 26.

The catheter 20, which is typically flexible and able to be pushed through the vasculature of the patient, has at its distal end 12 a dilator tip 34 of conventional form. Attached to the distal end of the catheter 20 is an inflatable balloon 36, which may be made of conventional balloon material with or without strengthening elements therein. The ends 38, 40 of the balloon are sealed to the outer surface of the catheter 20 in a fluid tight manner and specifically either side of the inflation/deflation port 24 such that the port is fluidly coupled to the chamber of the balloon. The balloon has a longitudinally compressed form, or doughnut shape, explained in further detail below. The port or ports 30, 32 are arranged so as to be located outside the zone of the balloon 36. In the embodiment of FIG. 1 there are shown two sets of ports 30, 32, a first set, of which two ports or holes are shown, is adjacent to the balloon 36, whereas the second set of holes or ports 32, again of which two are shown, is located at a spacing from the first set 30, in practice by distance which would be more than the length of a typical thrombus 42. This spacing could for example, be from a few centimeters up to about 20 centimeters. The holes or ports 30, 32 may be of the same size but in the preferred embodiment are of different sizes, namely with the proximal holes 32 being smaller than the distal holes 30. More particularly, the holes 30,32 are advantageously sized to ensure uniform injection of lytic fluid in the vessel, taking into account loss of fluid pressure at the distal holes 30 caused by earlier ejection of fluid through the proximal holes 32.

In FIG. 1, the two sets of ports 30 and 32 are shown substantially aligned in the longitudinal direction of the catheter 20 and extend in a common line. In other embodiments, though, the ports of each set 30, 32 may be alternatively or additionally angularly arranged around the catheter 20, thereby being able to administer lytic agent angularly around a patient's vessel 14 and thus entirely around a thrombus 42. It will be appreciated that such an embodiment would require provision of a different characteristic of lumen or chamber within the catheter 20 for feeding lytic agent to the angularly arranged holes or ports.

Figures 2, 7:
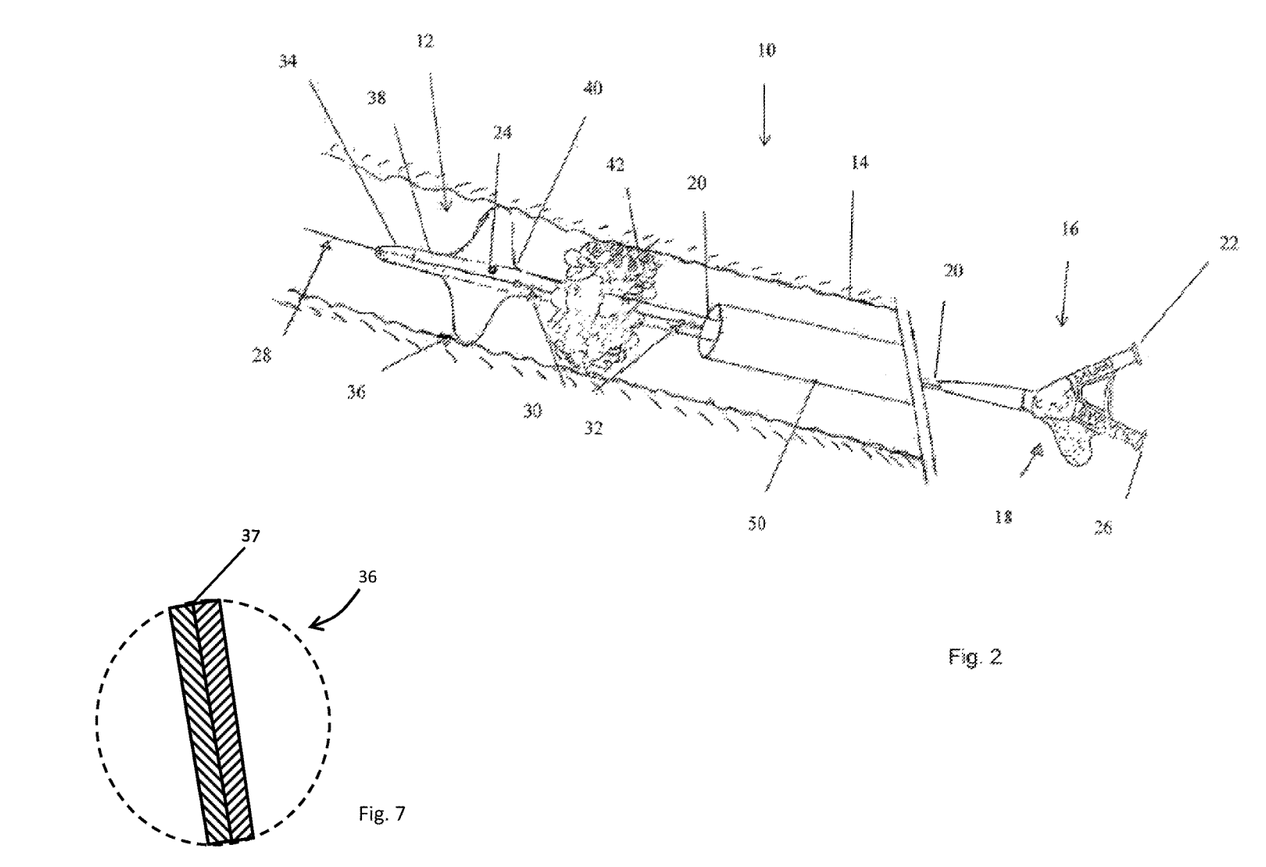
FIG. 2 is a schematic diagram of an elevational view of the thrombus removal apparatus showing an example of aspiration catheter.
FIG. 7 is a schematic cross sectional view of a portion of the balloon of the thrombus removal apparatus of FIG. 2.

Referring now to FIG. 2, there is shown another embodiment of thrombus removal apparatus, which in addition to the components in FIG. 1 is provided also with an aspiration catheter 50 which is disposed coaxially around the balloon or carrier catheter 20. The aspiration catheter 50 includes a proximal end (not shown) which extends to adjacent the Y-fitting 18, which in practice is coupled to an aspiration device. It is envisaged in some embodiments at least that the aspiration catheter 50 may be the outer carrier sheath of the introducer assembly, that is of the thrombus removal device.

Figure 3:
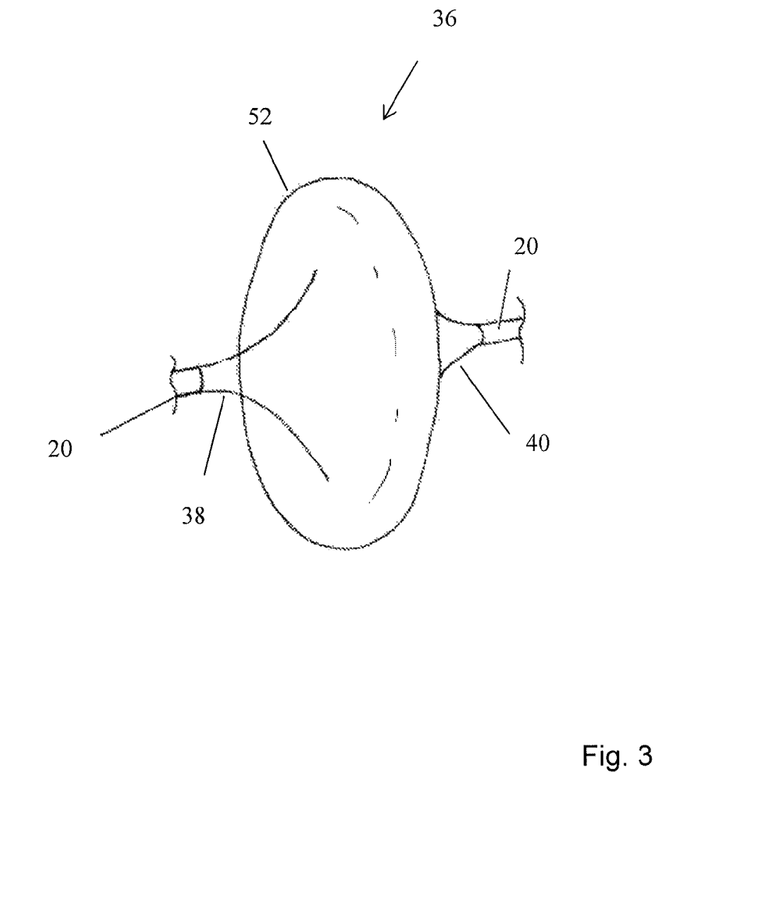
FIG. 3 is a schematic view of an embodiment of thrombus removal balloon.

Referring now to FIG. 3, there is shown a perspective of view of balloon 36 when inflated. The balloon 36 has what could be called a doughnut shape, being substantially flattened in the longitudinal direction when viewed with respect to the axis of the catheter 20. In other words, the axis of the catheter defines a longitudinal axis and the balloon has a diameter which is the same as or greater than a length of the balloon in a direction of the longitudinal axis. In the preferred embodiment the balloon 36 has a diameter which is the same as or greater than the length of the balloon as measured from the two ends of the balloon 38, 40. This contrasts with conventional balloons which are substantially longer than they are wide and intended generally to have specific inflated diameters at the body portion, which is substantially cylindrical when inflated. By contrast, the balloon 36 of the preferred embodiments disclosed herein has a shape which is rounded in a direction of the longitudinal axis. In addition, the balloon has a shape in which the radially outermost section 52 of the balloon 36 is rounded when viewed along the longitudinal axis of the balloon and balloon catheter 20. This shape enables the balloon 36, in practice, to press against the walls of the lumen 14 in all radial directions, even when these walls are not smooth or even and in particular also during the movement of the balloon 36 through a patient's lumen 14, as described in further detail below. The shape of the balloon 36 also can ensure that the balloon stays pressed against the lumen wall when the diameter of the lumen increases, as may occur in some uses of the assembly.

In an embodiment, the balloon 36 is of unitary size, that is there is provided a single balloon for a large range of lumen sizes. Advantageously, the balloon can inflate to fill a lumen of 2 to 26 millimeters in diameter. This can be achieved in part by the balloon being able to expand outwardly beyond its ends 38, 40 in a flattened configuration and in part by preferably making the balloon of a compliant material such as latex, silicone, polyurethane and the like. Most preferably, the balloon is made of a material which can stretch by up to or even more than 800% of its non-stretched diameter. These features, separately and in combination, allow for the balloon to be inflated by the appropriate amount to fill the vessel in which it is placed.

Figure 4:
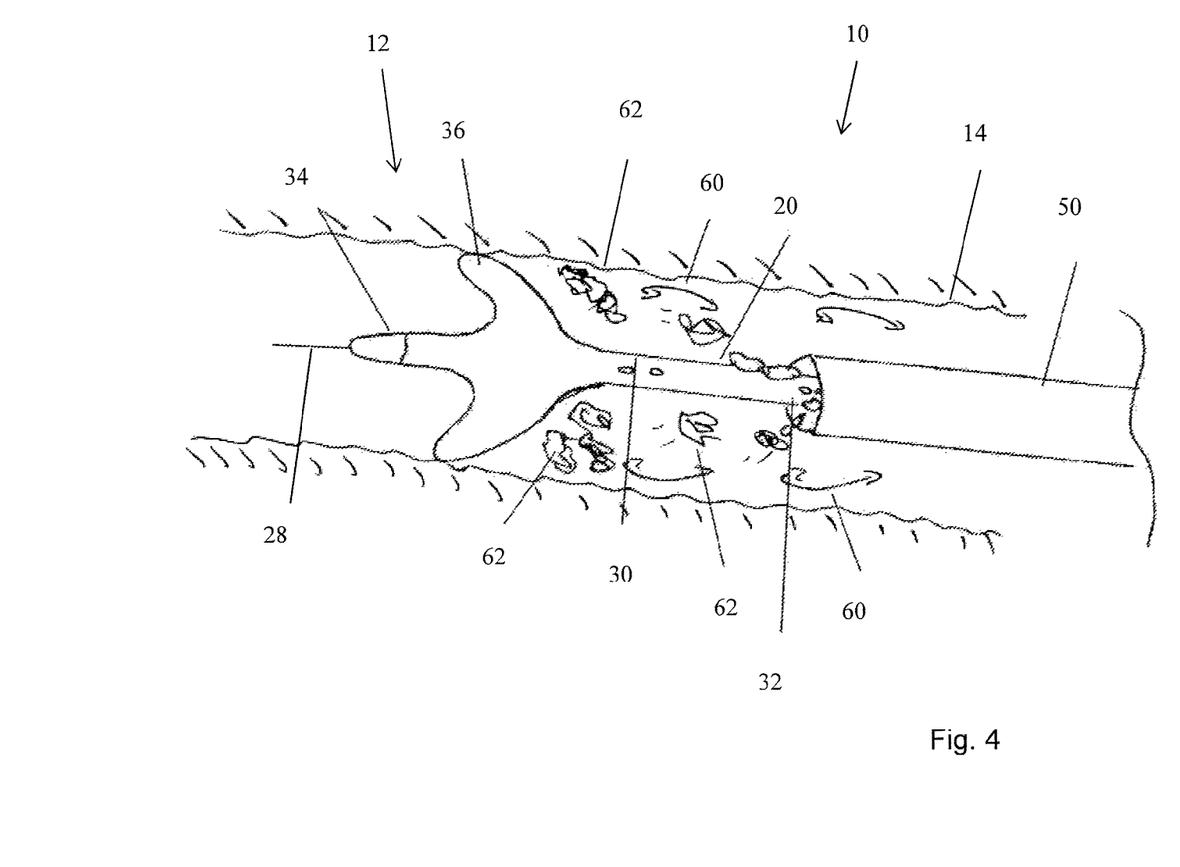
FIG. 4 is an elevational view of the embodiment of apparatus of FIG. 2 during the process of removal of a thrombus.

Referring now to FIG. 4, this shows in schematic form the embodiment of thrombus removal device of FIG. 2 during the process of removing a thrombus 42 from within a patient's vessel 14. For insertion into the patient's vasculature, the balloon is wrapped around the balloon catheter 20 in known manner and located within the sheath or catheter 50 during the deployment procedure. The wrapped balloon 36 and balloon catheter 20 are typically of a narrow diameter and able to be passed through a thrombus 42, following the guide of a preinstalled guide wire 28. The assembly 10 may be fed in a downstream direction, that is in the direction of flow of blood through the vessel 14. In this manner, the balloon 36 can occlude vessel 14 downstream of the thrombus 42. It is not excluded, however, that the balloon may be fed in an upstream direction and in fact this mode of use is most appropriate in some conditions. In some instances when the balloon is positioned upstream of the thrombus, there may be provided a filter located downstream of the balloon 36 in order to capture any large fragments of thrombus material.

When the distal end 12 of the balloon catheter 20 and the balloon 36 are positioned beyond the thrombus 42, the balloon 36 is inflated by means of inflation fluid passing through the Y-fitting 18 and into the balloon through the port or hole 24. The balloon 36 is inflated such that its outermost portions 52 press against the vessel wall.

The vessel upstream of the thrombus 42 is not occluded by the apparatus 10, that is there is no second balloon used to close off the vessel 14 from the other side of the thrombus 42. As a result, given the continuous pumping of blood in the patient's circulatory system, the movement of the patient's blood generates movement or turbulence in the volume of blood around the region of the thrombus 42, denoted by the arrows 60 in FIG. 4.

Once the balloon 36 has been inflated, lytic, specifically thrombolytic, fluid is pumped through the Y-fitting 18 and through the holes 30, 32 in the region of the thrombus 42. At this point, in some instances after a period allowing for weakening or partial breaking up of the thrombus 42, the catheter 20 is pulled in a proximal direction so as to drag the balloon 36 towards the thrombus 42 (an in practice in an upstream direction). The shape of the balloon 36 enables it to deform and ensures that it will remain properly in abutment against vessel wall 14. The scraping action of the balloon 36 assists in pulling thrombus material off the vessel wall 14 and in breaking up the thrombus 42 into fragments 62. The combination of allowing movement of blood within the vessel 14 around the thrombus 42 and the action of scraping thrombus material off the vessel wall 14 (all preferably under the effect of the lytic fluid administered around a thrombus) can substantially speed up the process of thrombus removal. Particularly, these actions prompt the creation of smaller thrombus fragments 62, many small enough to be able to be aspirated, but also increasing the surface area of thrombus material which is exposed to the lytic fluid.

The balloon 36 can be made of a single layer of material but may in other embodiments be strengthened, for instance by having one or more strengthening layers 37 of fibrous or woven material, as shown in FIG. 7.

Figure 5:
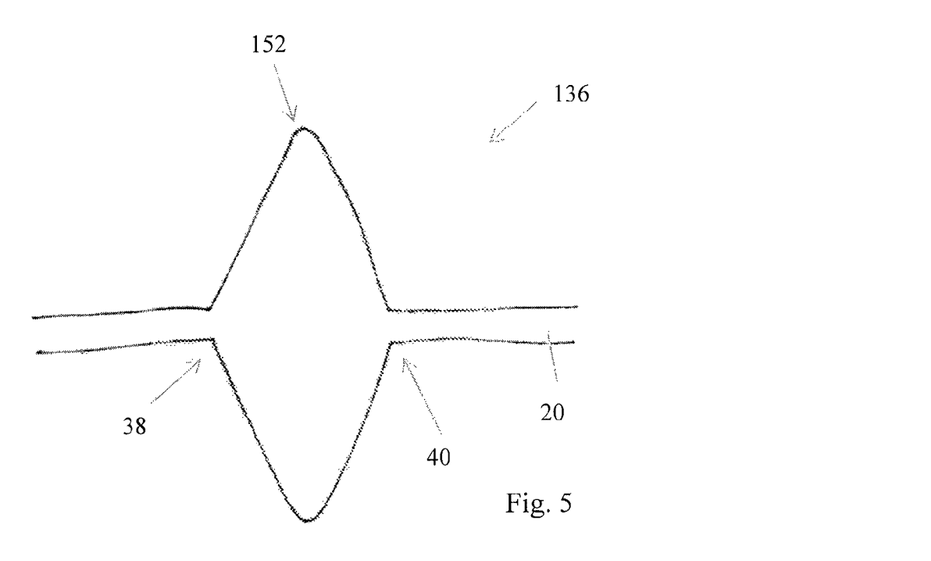
FIG. 5 is a schematic diagram of a side sectional view of an embodiment of thrombus removal balloon.
Figure 6:
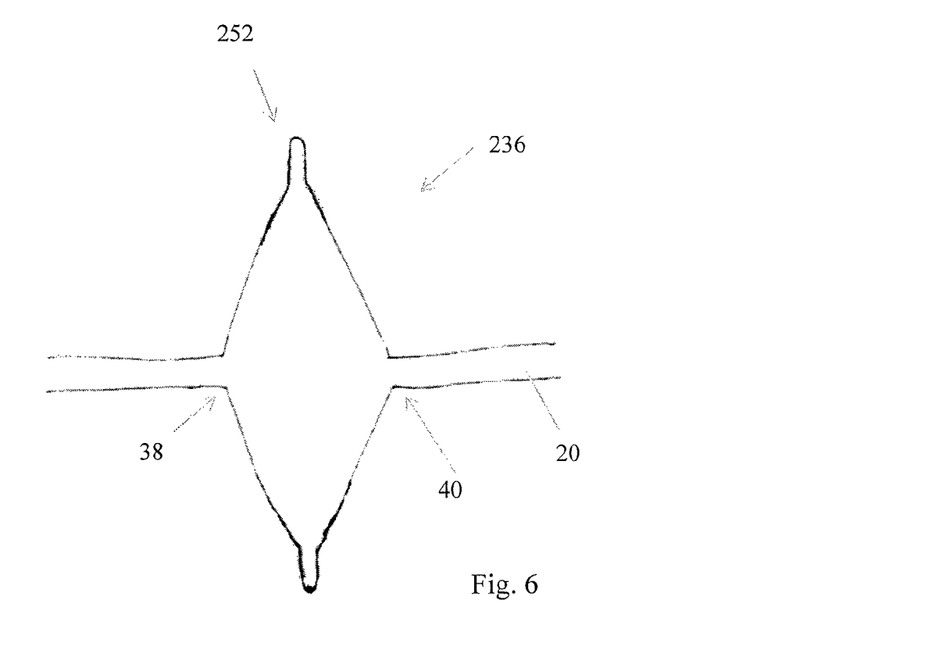
FIG. 6 is a schematic diagram of a side sectional view of an embodiment of thrombus removal balloon.

FIGS. 5 and 6 show balloons according to other embodiments of the invention. The descriptions of the shapes of balloons refer to the shapes of the balloons when inflated and not distorted.

FIG. 5 is a schematic diagram of a side sectional view of thrombus removal balloon 136 according to an embodiment of the invention. The balloon 136 can be used in place of the balloon 36 in the arrangements described above. Accordingly, the features of this embodiment of the invention can be as per the embodiments described above, except as indicated below. As in embodiments described above, the carrier catheter 20 defines a longitudinal axis for the balloon 136. A length of the balloon in a direction of the longitudinal axis is less than a diameter of the balloon. In the shown embodiment, the longitudinal length is the distance as measured between the two ends of the balloon 38, 40 where it is sealed to the catheter 20.

A radius of the balloon 136 tapers from a radially outermost section 152 towards the ends 38, 40 of the balloon. The radius of the balloon at any point along the longitudinal axis can be considered to be the distance of the wall of the balloon from the longitudinal axis in a direction transverse to and preferably perpendicular to the longitudinal axis. In other words, therefore, the radius of the balloon decreases in both longitudinal directions as one moves away from the radially outermost section 152. As can be seen from FIG. 5, the radially outermost section 152 is between the ends 38, 40, preferably substantially mid-way between the ends 38, 40.

The taper is preferably a linear taper. That is to say that the radius of the balloon tapers in a substantially linear fashion from the radially outermost section 152 to each of the ends 38, 40 so the balloon is substantially diamond shaped in cross-section. However, as in embodiments discussed above, the radially outermost section 152 is rounded in a direction of the longitudinal axis.

FIG. 6 shows a schematic diagram of side sectional view of a balloon 236 according to another embodiment of the invention. This embodiment corresponds to the embodiment of FIG. 5, except that at the radially outermost section 252, there is provided a circumferential flange, which is preferably rounded in the direction of the longitudinal axis. The circumferential flange is integral with the balloon. Furthermore, the flange is inflatable and is part of the balloon 236 so that the balloon 236 and the flange enclose a single inflatable chamber. This means that as the balloon 236 is inflated, the flange is also inflated. The thickness of the wall of the flange is the same as the thickness of the wall of the balloon 236.

In all embodiments, it is preferable to minimise the contact of the balloon with the wall of a vessel. This can reduce the resistance to movement along the vessel wall. Furthermore, it can enable the apparatus to be used in cerebrovascular surgery In the embodiment of FIGS. 5 and 6, the contact with the wall is minimised and the scraping action is improved by providing a balloon with a relatively pointed radially outermost section. The shapes of the balloons 136, 236 still allow them to deform to ensure they remain properly in abutment against a vessel wall. In particular, in the embodiment of FIG. 6, the flange effectively acts as a scraper along a vessel wall, assisting with removing thrombus material from the vessel wall, breaking up the thrombus, and ensuring that fragments of the thrombus do not pass the balloon and fail to be collected.

The balloons described herein are compliant in order that they can maintain contact with a vessel wall as they are dragged along the vessel wall, without being damaged.

As described above, the shape of the balloon of embodiments of the invention is advantageous for providing an effective scraping action for removing thrombi from the walls of vessels. However, in some embodiments, an over-inflated balloon can be distorted so as to lose its advantageous shape. To prevent this, in embodiments of the invention, a thrombus removal apparatus is provided as a kit. The kit includes a delivery sheath, such as the delivery sheath 50 as shown in FIG. 2. As described above, the delivery sheath can also serve as an aspiration catheter. The kit also includes a plurality of carrier catheters 20. The carrier catheters 20 can be as described in any of the above embodiments. However, preferably, each of the carrier catheters includes a balloon such as that shown in FIG. 5 or 6. Each of the carrier catheters includes a balloon of the same shape, but of different sizes. By being different sizes, what is meant is that when the balloons are inflated, they have different diameters. However, it can also mean that the longitudinal lengths of the balloons are different as well.

Such a kit means that the medical practitioner can select the carrier catheter which has a balloon matched to the size of the vessel into which it is to be inserted. In this way, the practitioner can avoid using a balloon that is too small for a vessel, which might otherwise risk the balloon over-inflating and losing its advantageous shape.

The balloon of embodiments of the invention may have a smooth outer surface but other embodiments may include one or more scoring or cutting elements. The scoring elements can be a region of thicker material. In some embodiments, the scoring elements are arranged to face in the direction in which the balloon will be dragged when inflated. This is to take into account and to compensate for the fact that the balloon will effectively be pulled back by the wall of the vessel as it is dragged.

The structure of the apparatus 10 enables it to be used in different modes of operation, particularly useful for treating thrombi of different character, including for instance less well-established thrombi which have looser structures, smaller thrombi, thrombi which are attached only loosely attached to the vessel wall and so on. Specifically, the apparatus 10 can be operated without inflating the balloon 36 and only by administration of lytic agent through the ports 30, 32; or by use of a scraping action of the balloon 36 without administration of lytic agent, for example. Similarly, the apparatus 10 could be operated in a different sequence, for instance by administration of lytic agent prior to inflation of the balloon 36. In other words, the apparatus 10 can be operated differently in dependence upon the particular medical requirements of a patient.

The apparatus 10 and method disclosed herein are suited for treating thrombi in any part of a patient's circulatory system, particularly for the venous area, particularly the venous fistula as well as in the iliac regions.

It will be appreciated that the above described embodiments of the present invention and the teachings herein are broader than the specific embodiments. It is also to be appreciated that the features of the various embodiments may be combined with one another. Similarly, the claims, although set out in single dependent form, are to be treated as combinable as if they were set out in multiple dependent form.

The disclosures of British patent application number GB1121788.2, from which this application claims priority, and in the abstract accompanying this application, are incorporated herein by reference.

The invention claimed is:

1. Thrombus removal apparatus for removing a thrombus from a vessel in a patient's vasculature, the apparatus including:
a carrier catheter having a distal end and a proximal end and defining a longitudinal axis;
a singular occlusion device fixed to or proximate the distal end of the catheter;
at least one supply element located proximal of said distal end of the carrier catheter for supplying a bioactive agent; and
a retrieval element located proximal of said distal end of the carrier catheter for retrieving thrombus material from a patient's vasculature, the retrieval element retrieving thrombus material without occluding the vasculature proximal the thrombus;
wherein the occlusion device includes a balloon having an outer surface, the balloon forming a first seal with the catheter at a first end of the balloon and a second seal with the catheter at a second end of the balloon defining a length from the first end to the second end in the direction of the longitudinal axis, the balloon being expandable to occlude the vessel solely at or proximate said distal end of the carrier catheter,
wherein the balloon is rounded in the direction of the longitudinal axis and has a longitudinally compressed form such that when inflated the balloon has a diameter which is greater than the length, and
wherein the outer surface of the balloon includes one or more scoring elements comprising a region of thickened material, which scrape the thrombus from the vessel when the inflated balloon is drawn proximally.

2. Thrombus removal apparatus according to claim 1, wherein the balloon is made of a material which can stretch by at least 800% of its non-stretched diameter.

3. Thrombus removal apparatus according to claim 1, wherein the balloon is designed to scrape against a vessel wall when inflated thereby to scrape thrombi from the vessel wall.

4. Thrombus removal apparatus according to claim 1, wherein the balloon includes a plurality of layers, wherein each layer of the plurality of layers comprises a material selected from the group consisting of a fibrous material and a woven material.

5. Thrombus removal apparatus according to claim 1, wherein the one or more scoring elements are arranged to face in a direction in which the balloon will be drawn.

6. Thrombus removal apparatus according to claim 1, wherein the at least one supply element comprises at least two supply elements substantially aligned along the longitudinal axis of the carrier catheter and wherein a proximal supply element of the at least two supply elements is smaller than a distal supply element of the at least two supply elements.

7. Thrombus removal apparatus according to claim 1, wherein the carrier catheter includes at least one fluid supply lumen for supplying bioactive agent in fluid form to the port or ports.

8. Thrombus removal apparatus according to claim 1, wherein the balloon is compliant.

9. Thrombus removal apparatus according to claim 8, wherein the balloon is made of latex, silicone or polyurethane.

10. Thrombus removal apparatus according to claim 1, wherein the supply element includes at least one port in the carrier catheter.

11. Thrombus removal apparatus according to claim 10, wherein a plurality of ports are spaced at least one of: longitudinally along the carrier catheter and angularly around the catheter.

12. Thrombus removal apparatus according to claim 1, wherein the retrieval element is an aspiration catheter.

13. Thrombus removal apparatus according to claim 12, wherein the aspiration catheter is moveable relative to the carrier catheter.

14. Thrombus removal apparatus according to claim 13, wherein the carrier catheter and the aspiration catheter are concentrically arranged, the aspiration catheter being located over the carrier catheter.

15. Thrombus removal apparatus according to claim 14, wherein the carrier catheter is able to be located substantially entirely within the aspiration catheter.

16. Thrombus removal apparatus according to claim 15, wherein the aspiration catheter acts as a delivery sheath for the endoluminal positioning of the carrier catheter.

* * * * *